US007297940B2

(12) United States Patent
Bern

(10) Patent No.: US 7,297,940 B2
(45) Date of Patent: Nov. 20, 2007

(54) METHOD, APPARATUS, AND PROGRAM PRODUCT FOR CLASSIFYING IONIZED MOLECULAR FRAGMENTS

(75) Inventor: Marshall W. Bern, San Carlos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 309 days.

(21) Appl. No.: 11/121,199

(22) Filed: May 3, 2005

(65) Prior Publication Data

US 2006/0249669 A1 Nov. 9, 2006

(51) Int. Cl.
*B01D 59/44* (2006.01)
*H01J 59/44* (2006.01)
(52) U.S. Cl. .......................... 250/282; 436/89; 436/90; 436/96; 436/94; 436/173; 703/11; 703/12; 702/23; 702/27; 702/19; 702/22; 702/20; 702/76; 702/32; 702/194; 503/334; 503/335; 503/336; 503/337
(58) Field of Classification Search ................ 250/282; 436/89, 90, 96, 94, 173; 702/19, 22, 23, 702/27, 20, 32, 76, 194; 703/11, 12; 503/334, 503/335, 336, 337
See application file for complete search history.

(56) References Cited

U.S. PATENT DOCUMENTS 5,538,897 A * 7/1996 Yates et al. .................... 436/89
6,017,693 A * 1/2000 Yates et al. ...................... 435/5
6,582,965 B1 * 6/2003 Townsend et al. ............. 436/89
6,963,807 B2 * 11/2005 Townsend et al. ............. 702/27
2006/0136158 A1 * 6/2006 Goldberg et al. ............. 702/76

OTHER PUBLICATIONS

D. Harel and Y. Koren, A Fast Multi-Scale Mehtod for Drawing Large Graphs, Journal of Graph Algorithms and Applications, vol. 6 (2002), No. 3, 179-202.*
Kenneth G. Standing, *Peptide And Protein De Novo Sequencing By Mass Spectrometry*, Current Opinion in Structural Biology 2003, 13:595-601.
Sandrine Uttenweiler-Joseph, Gitte Neubauer, Savvas Christoforidis, Marino Zerial & Matthias Wilm, *Automated De Novo Sequencing Of Proteins Using The Differential Scanning Technique*, Proteomics 2001, 1,668-682.
J. Alex Taylor & Richard S. Johnson, *Implementation And Uses Of Automated De Novo Peptide Sequencing By Tendem Mass Spectrometry*, Anal. Chem. 2001, 73, 2594-2604.
Ting Chen, Ming-Yang Kao, Matthew Tepel, John Rush & George M. Church, *A Dynamic Programming Approach To De Novo Peptide Sequencing Via Tandem Mass Spectrometry*, Journal Of Computational Biology, vol. 8, 2001, 325-337.
Bin Ma et al., *An Effective Algorithm For The Peptide De Novo Sequencing From MS/MS Spectrum*, Symp. Comb. Pattern Matching, 2003, 266-278.
Olaf Lubeck et al., *New Computational Approaches For De Novo Peptide Sequencing From MS/MS Experiments*, Proceedings Of The IEEE, vol. 90, 2002, 1868-1874.

(Continued)

*Primary Examiner*—Jack Berman
*Assistant Examiner*—Meenakshi Sahu
(74) *Attorney, Agent, or Firm*—Fay Sharpe LLP

(57) ABSTRACT

Apparatus, methods, and program products are disclosed that classify spectral peaks in dissociation spectrum data and thereby improves the efficiency of molecular sequencing.

28 Claims, 11 Drawing Sheets

OTHER PUBLICATIONS

Robert M. Day et al., *PPM-Chain-De Novo Peptide Identification Program Comparable In Performance To Sequest*, Proc. IEEE Computational Systems Bioinformatics, 2004, 505-508.

Bo Yan et al., *Separation Of Ion Types In Tandem Mass Spectrometry Data Interpretation—A Graph-Theoretic Approach*, Proc. Computational Systems Bioinformatics, 2004, 236-244.

* cited by examiner

METHOD, APPARATUS, AND PROGRAM PRODUCT FOR CLASSIFYING IONIZED MOLECULAR FRAGMENTS

BACKGROUND

1. Field

This technology relates to the field of identifying a complex molecule having a structure that includes molecular subunits bound together at cleavage sites through the analysis of fragmentation spectra of the complex molecule.

2. Background

There are a number of techniques that can be used to identify complex molecules. Some of these techniques use fragmentation spectra of the complex molecules. Such fragmentation spectra can be generated by Tandem Mass Spectrometry ("MS/MS") techniques as is well known in the art. Analysis of the fragmentation spectra can provide clues to the structure and the sequence of molecular subunits that make up the complex molecule.

An ideal spectrum would contain a complete "ladder" of b-ions or y-ions from which we could simply read off the molecular subunit sequence or its reversal. Hence generation of candidate sequences is usually formulated as a longest (or best) path problem in a peak graph, which has a vertex for each peak in the spectrum and an edge connecting two peaks if they differ by the mass of a possible molecular subunit. Due to missed cleavages, peak graphs might use vertices corresponding to small mass ranges rather than peaks, and/or include edges between vertices differing by the mass of a pair of residues.

One way to identify the structure of a complex molecule is to identify and score candidate sequences for the complex molecule in light of the fragmentation spectra. In one approach, the candidates can be found in a database of known molecules. U.S. Pat. No. 5,538,897 to Yates, III et al. (hereby incorporated by reference in its entirety) teaches such a method where the complex molecule is a protein or peptide. The difficulty with this approach is that the complex molecule needs to have been previously identified or predicted and its characteristics stored in the database. Thus, a fragmentation spectrum for a complex molecule that has not been previously characterized and entered into the database will not be identified.

Another way to identify the structure of a complex molecule is to use the de novo sequencing approach. A method for sequencing peptides or proteins taking this approach is disclosed by U.S. Pat. No. 6,582,965 to Townsend et al. (hereby incorporated by reference in its entirety). In the de novo sequencing approach, the method attempts to generate all possible sequences of molecular subunits that could be consistent with the fragmentation spectrum. One problem with the de novo sequencing approach for proteins and peptides is that it is difficult to determine which peaks are y-ions (c-terminus fragments) and which peaks are b-ions (n-terminus fragments). The term "b/y ambiguity" identifies this difficulty. This difficulty is compounded because the fragmentation spectrum includes spectral peaks for noise (ions that are not fragments of the parent molecule) as well as spectral peaks for signals (ions that are fragments of the parent molecule). Noise in the fragmentation spectra decreases the probability of correctly sequencing a complex molecule from fragmentation spectra.

Furthermore, it is very rare for a peptide spectrum to have a complete ladder of b- or y-ions, and hence most sequencers attempt to form a ladder from a mixture of the two types. Lutefisk (see *Implementation anduUses of Automated De Novo Peptide Sequencing by Tandem Mass Spectrometry*, by Taylor et al. (Anal. Chem., 73 (2001), 2594-2604)) turns each peak into two vertices, one at the observed mass and the other at the complementary mass. Such complementation has two drawbacks: in effect it adds many noise peaks, and it allows the use of a single peak as both a b- and a y-ion. A paper entitled *A Dynamic Programming Approach to De Novo Peptide Sequencing by Mass Spectrometry*, by Chen et al. (J. Computational Biology, 8 (2001), 325-337) showed how to correct the latter drawback with a longest-path algorithm that disallows the simultaneous use of both vertices from a single peak. A paper entitled *An Effective Algorithm for the Peptide De Novo Sequencing from MS/MS Spectrum*, by Ma et al. (Symp. Comb. Pattern Matching, 2003, 266-278) teaches a more subtle fix; they allow the simultaneous use of both vertices, but do not score the peak twice. None of these solutions, however, addresses the larger drawback—doubling the number of noise peaks.

A paper entitled *New Computational Approaches for De Novo Peptide Sequencing from MS/MS Experiments*, by Lubeck et al., (Proc. IEEEV 90, (2002), 1868-1874) proposed the idea of classifying peaks as b-, y-, or "other" prior to running the longest-path algorithm. The longest-path algorithm would use the peak classifications and would avoid complementing every peak. Lubeck did not disclose algorithms or results.

A paper entitled *PPM-Chain—De Novo Peptide Identification Program Comparable in Performance to Sequest*, by Day et al., (Proc. IEEE Computational Systems Bioinformatics, 2004, 505-508) independently proposed peak classification (as an alternative rather than as an adjunct to the longest-path algorithm), and built a three-class classifier keying on b/y pairs and the "neutral loss neighborhood" (about 30 Daltons) around each peak.

A paper entitled *Separation of Ion Types in Tandem Mass Spectrometry Data Interpretation—A Graph-Theoretic Approach*, by Yan et al., (Proc. IEEE Computational Systems Bioinformatics, 2004, 236-244) disclosed the same idea and formulated the classification problem as a graph tripartition problem. They disclosed an exponential-time algorithm for an exact solution to the problem.

Thus, it would be advantageous to find a method that is able to classify spectral peaks in the fragmentation spectra as b-ions and y-ions with weights for classification confidence, without increasing the noise in the fragmentation spectra and that uses a less computationally demanding algorithm than Yan et al.

DESCRIPTION OF THE PREFERRED EMBODIMENTS

Figure 1:
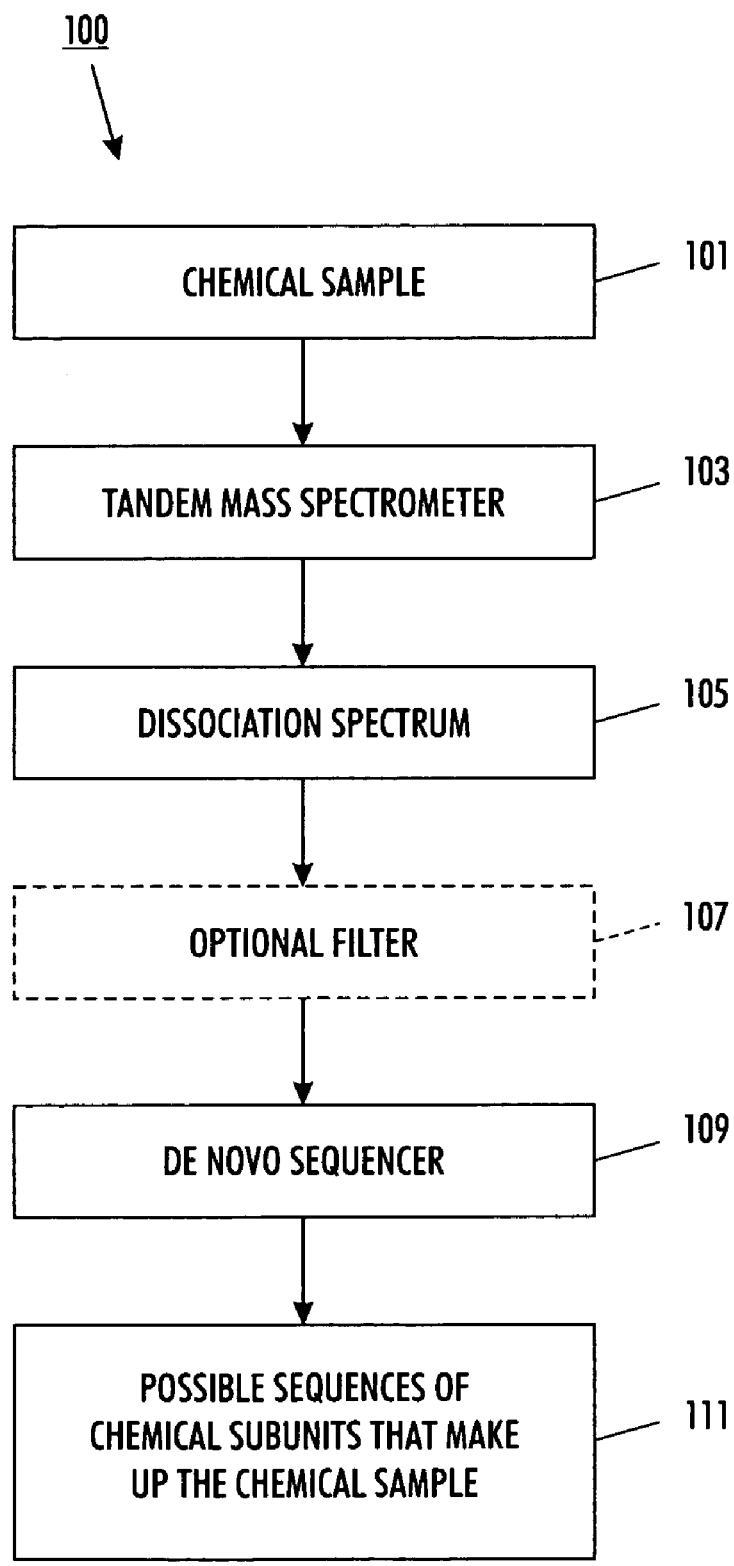
FIG. 1 Illustrates a molecular sequencing system.

The following 'notations and nomenclature' are provided to assist in the understanding of the presented technology and embodiments thereof.

Programmed routine or function—A programmed routine or a programmed function is a sequence of program code, in any programming methodology, that can be invoked, with or without parameters, to perform its designed operation responsive to any provided parameters, accessible state, and/or accessible data. A programmed routine or function can be instructions that are processed by general purpose CPU or other electronics. A programmed function generally returns a value. A programmed routine or function can often be implemented in electronics designed to perform the designated operation and can provide result values either with digital values, analog values, or a combination of digital and analog values.

Present, presented, presenting—The result of the operation of embodiments of the technology described herein can be "presented" by the embodiment. This can include storing representations of a spectrum with spectral peaks identified by the use of the technology or displaying data from such a spectrum; displaying or storing molecular sequences identified by the use of the technology; passing data representing or derived from the use of the technology to another system (for example, a computer via use of a computer-usable data carrier such as tangible storage devices or a network—and/or using remote procedure call protocols), to another procedure, and/or to a programmed routine.

Procedure—A procedure is a self-consistent sequence of computerized steps that lead to a desired result. These steps can be defined by one or more computer instructions. These steps can be performed by a computer executing the instructions that define the steps. Thus, the term "procedure" can refer (for example, but without limitation) to a sequence of instructions, a sequence of instructions organized within a programmed-procedure or programmed-function, or a sequence of instructions organized within programmed-processes executing in one or more computers. Such a procedure can also be implemented directly in specialized circuitry that performs the steps.

The inventor has developed apparatus, methods, and program products that classify spectral peaks in dissociation spectrum data and thereby improves the efficiency of molecular sequencing. This is accomplished by accessing dissociation spectrum data that includes spectral peaks representing fragments of a parent molecule. The parent molecule includes molecular subunits and cleavage sites wherein each of the cleavage sites connects a first one of the molecular subunits and a second one of the molecular subunits. The spectral peaks are associated with peak intensities. Some of the spectral peaks are selected to be represented by corresponding vertices. Weighted edges are assigned to the corresponding vertices and then a confidence-weighted classification is applied to corresponding vertices responsive to the weighted edges. Once the vertices are classified, the peak intensities can be adjusted responsive to the classification and the peak intensities are presented.

The inventor has realized that classifying peaks as b-ions, y-ions and "others", is unnecessary to improve de novo analysis. When using classification in conjunction with the longest-path algorithm, it suffices to solve a much easier problem: divide the peaks into two groups, such that one group contains all the b-ions and the other contains all the y-ions. Such a bipartition allows one group to be complemented (subtracted from the parent ion mass) and thereby removes the b/y ambiguity of peaks without doubling the number of noise peaks. The inventor applies spectral graph partitioning—a polynomial-time algorithm—to this bipartition problem. By using a polynomial-time algorithm instead of an exponential-time algorithm, much more complex spectra can be classified.

FIG. 1 illustrates operation of a molecular sequencing system 100. In such a system, a chemical sample 101 is input to a tandem mass spectrometer 103 that generates a dissociation spectrum 105 (see FIG. 3). The dissociation spectrum 105 can be filtered by an optional spectrum filter 107 to pass high quality spectra to a de novo sequencer 109 that processes the dissociation spectrum 105 to determine a possible sequence of chemical subunits 111 of the chemical sample 101 that can be presented.

One skilled in the art will understand that a tandem mass spectrometer generates the dissociation spectrum data by selecting parent molecules having a specific molecular mass (within a tolerance) in a first stage of the tandem mass spectrometer, causing the selected parent molecules to be fragmented at cleavage sites (using methods known to one skilled in the art), and accumulating the count of the resulting fragments in m/z histogram bins. A number of bins can represent a single spectral peak. Either the height or the area of the spectral peak will be referred to as the spectral peak's "intensity".

Figure 2:
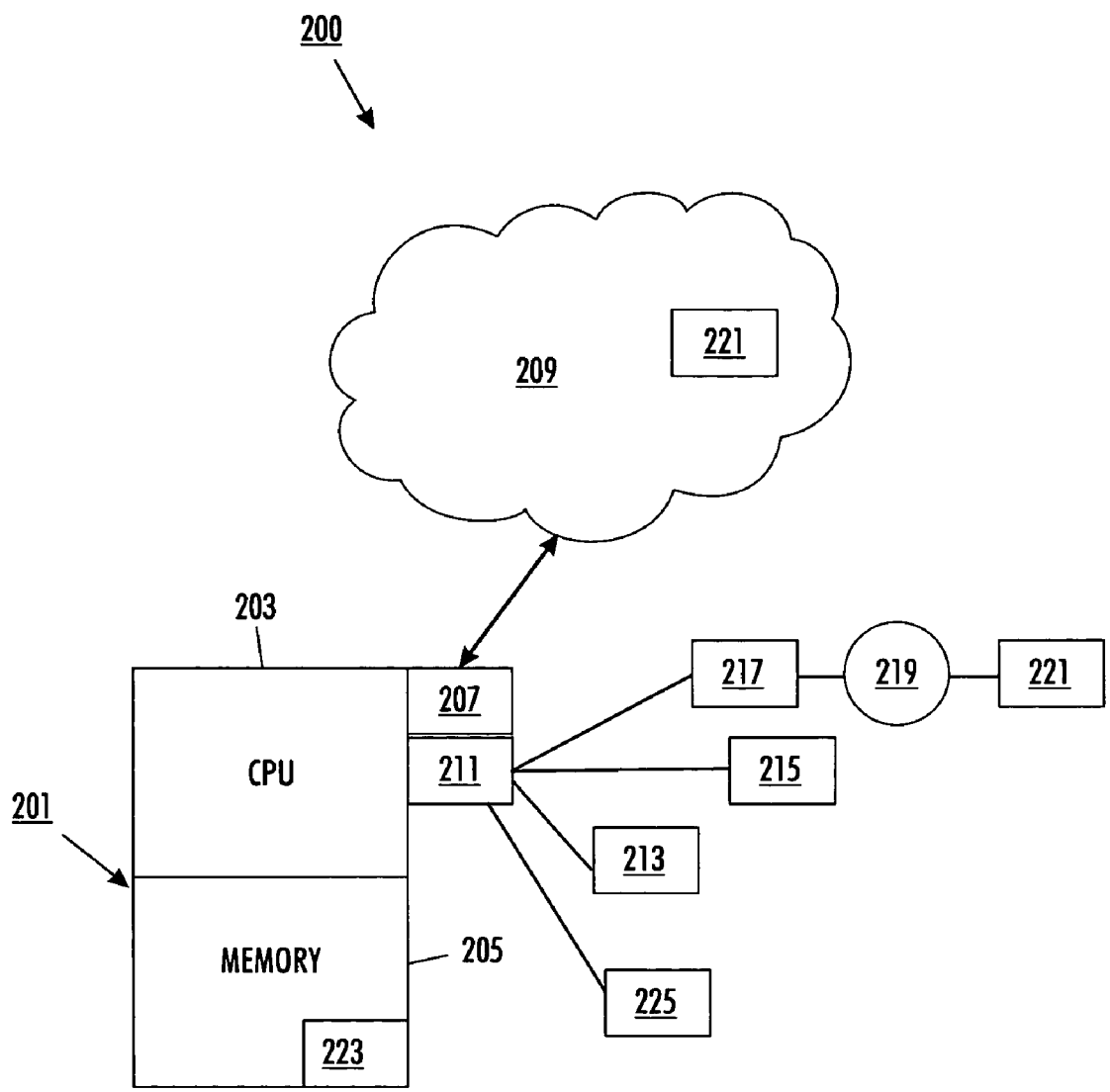
FIG. 2 illustrates a computer system in accordance with a preferred embodiment.

FIG. 2 illustrates a computer system 200 that can incorporate the disclosed technology. The computer system 200 includes a computer 201 that incorporates a CPU 203, a memory 205, and, in some embodiments, a network interface 207. The network interface 207 provides the computer 201 with access to a network 209. The computer 201 also includes an I/O interface 211 that can be connected to a user interface device(s) 213, a storage system 215, and a removable data device 217. The removable data device 217 can read a tangible computer-usable data carrier 219 that typically contains a program product 221. The storage system 215 (along with the removable data device 217), the tangible computer-usable data carrier 219 and any network file storage comprise a file storage mechanism. The tangible computer-usable data carrier 219 can be a ROM within the computer system 200, within replaceable ROM, a memory stick, CD, floppy, DVD or any other tangible media. The program product 221 accessed from the tangible computer-usable data carrier 219 is generally read into the memory 205 as a program 223 that instructs the CPU to perform the processes described herein as well as other processes. In addition, the program product 221 can be provided from the network (generally encoded within an electromagnetic carrier wave—including light, radio, and electronic signaling) through the network interface 207. One skilled in the art will understand that the network 209 is another computer-usable data carrier.

A tandem mass spectrometer 225 can be in direct communication with the I/O interface 211 and can provide dissociation spectrum data directly to the computer 201 (for example, by using a data bus (for example a USB, FireWire®, or custom connection). In addition, the tandem mass spectrometer 225 can provide dissociation spectrum data over the network 209, or via the tangible computer-usable data carrier 219. One skilled in the art will understand that not all of the displayed features of the computer 201 need to be present for all embodiments.

Figure 3:
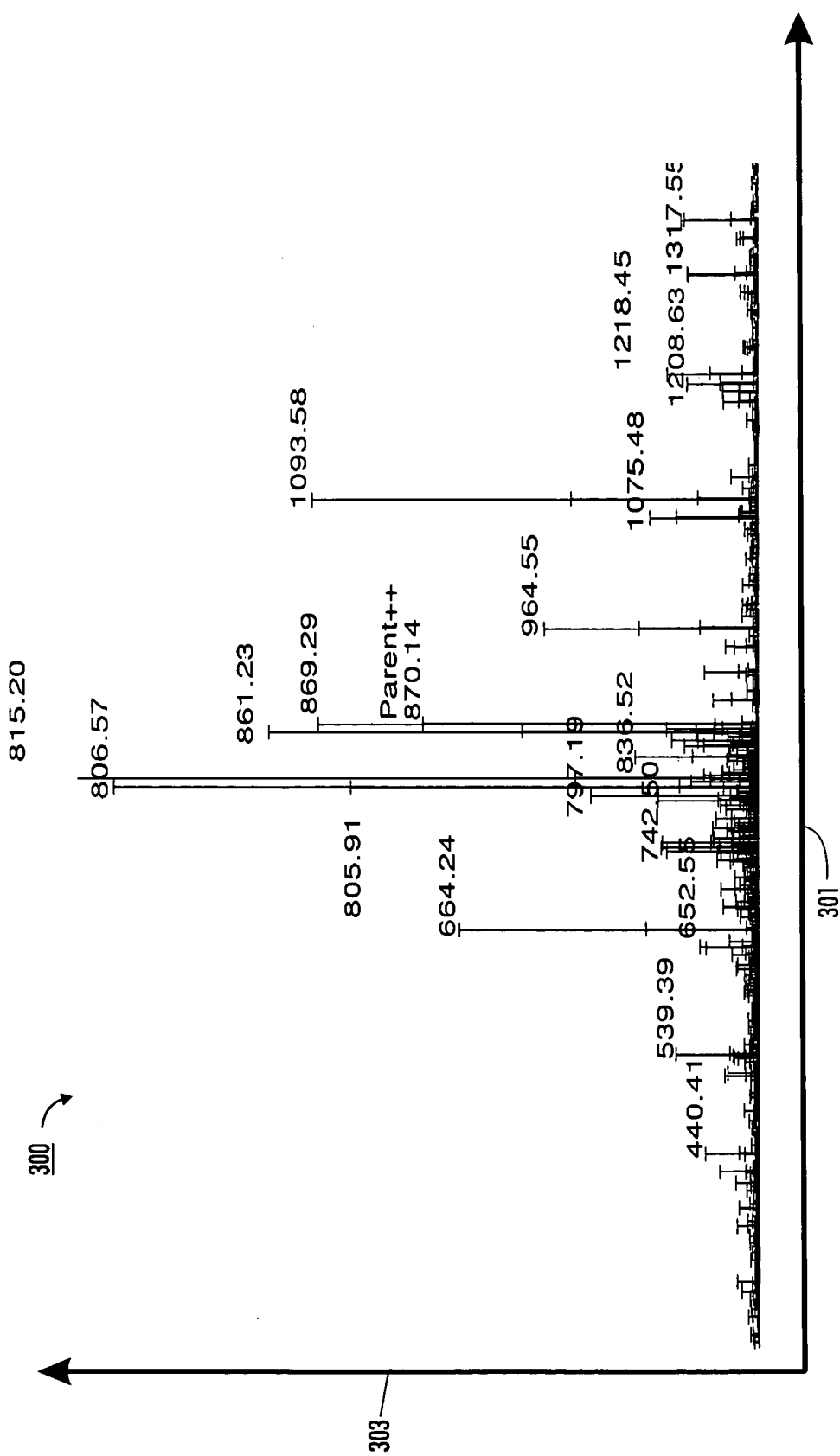
FIG. 3 illustrates a histogram of an example dissociation spectrum that can be produced by a tandem mass spectrometer and that indicates the number of ions observed at each m/z value.

FIG. 3 illustrates an example tandem mass spectrometer dissociation spectrum 300 of a parent molecule plotted on an x-axis in m/z 301 and a y-axis in intensity 303. The parent molecule generally includes a number of molecular subunits connected by cleavage sites. The tandem mass spectrometer generally disassociates many of the parent molecules into at least two fragments at any of the cleavage sites. The dissociation spectrum data indicate the number of fragments produced having similar m/z. The location of the spectral peak on the x-axis in m/z 301 represents the mass of a singly charged ion. The term intensity refers to the height or area of the spectral peak. The intensity of a spectral peak indicates how often the parent molecules have been fragmented at a particular cleavage site. The m/z, intensity, structure, and shape of the spectral peak are some of the characteristics of the spectral peak.

The tandem mass spectrometer often provides annotation information for the spectral peaks such as the m/z for selected intense spectral peaks. It can also detect doubly charged parent molecules. As previously discussed, one difficulty with this representation is that it is very difficult to determine noise peaks from dissociation (or fragmentation) spectral peaks. In the case of peptides and proteins, it is very difficult to determine which spectral peaks indicate b-ions, y-ions, a-ions, or noise. One skilled in the art will understand one of the very significant problems in protein and/or peptide sequencing is that of determining whether a spectral peak represents a y-ion, a b-ion, or noise. This is the b/y ambiguity problem.

Figure 4:
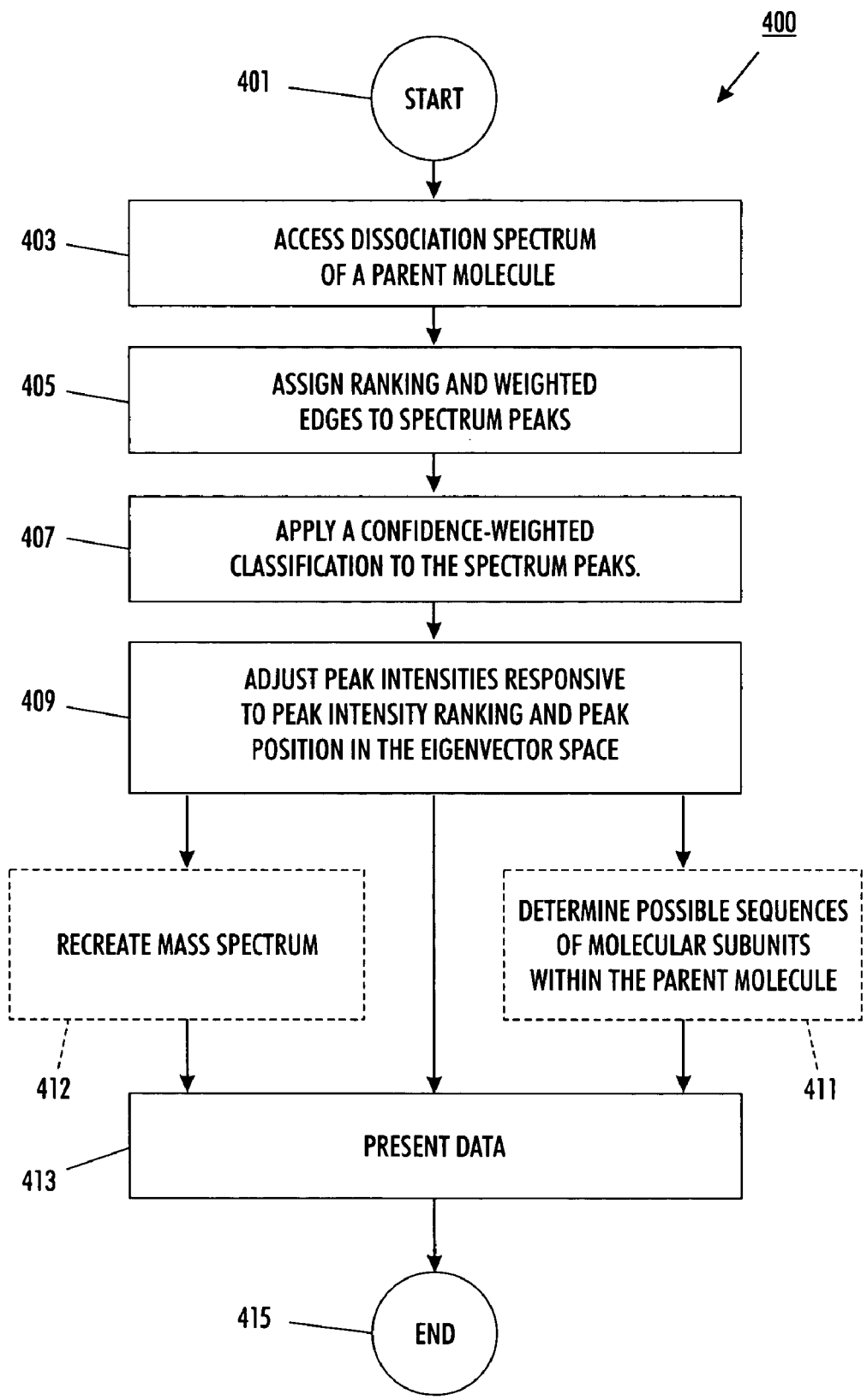
FIG. 4 illustrates one embodiment of a molecular fragment classification process.

FIG. 4 illustrates a molecular fragment classification process 400 that can be used as, or by the de novo sequencer 109 to determine one or more possible sequences of molecular subunits that make up a parent molecule. The molecular fragment classification process 400 initiates at a 'start' terminal 401 and continues to an 'access dissociation spectrum data' procedure 403 that accesses the dissociation spectrum data. The dissociation spectrum data can be accessed from the storage system 215, the network 209, the tangible computer-usable data carrier 219, or directly from the tandem mass spectrometer 225 or by any other data access technique or technology. The dissociation spectrum data includes spectral peaks. The spectral peaks have intensities, which are initially related to ion counts but may be changed responsive to subsequent computations.

The parent molecule may be a protein, peptide, lipid, polymer (composed of a single monomer, or multiple monomers), glycan, etc. Much of the rest of this description is cast in the context of peptides and amino acids. However, one skilled in the art will understand that the techniques taught herein can be applied to other molecules that have molecular subunits connected by cleavage sites.

Once the dissociation spectrum data is accessed, an 'assign ranking and weighted edges to spectral peaks' procedure 405 processes the dissociation spectrum data to identify the m/z (mass) and intensity of the spectral peaks, select the relevant spectral peaks, and ranks the spectral peaks in intensity order (irank). One skilled in the art will understand that the spectral peak data in the dissociation spectrum data is generally not directly manipulated, but rather the spectral peaks' characteristics are obtained from the dissociation spectrum data and used to establish values in data structures (often termed vertices herein) that represent the characteristics of the spectral peaks.

The 'assign ranking and weighted edges to spectral peaks' procedure 405 also initializes a data structure called a spring system that establishes weighted edges between the vertices that represent the spectral peaks. Some embodiments can insert artificial vertices into the array and provide weighted edges between the artificial peaks and some or all of the spectral peak vertices. The array created by the 'assign ranking and weighted edges to spectral peaks' procedure 405 is analogous to a physical spring system in which the intensity of a peak is analogous to a mass and the weighted edge is analogous to a spring that provides a repulsion/attraction force between the peaks connected by the weighted edge. The inventor believes that this is the first application of a spring system to dissociation spectrum data. The 'assign ranking and weighted edges to spectral peaks' procedure 405 is subsequently described with respect to FIG. 5.

Once the spring system data structure is created, an 'apply confidence-weighted classification to the spectral peaks' procedure 407 applies a confidence-weighted classification process to the spring system represented by the data structure. This generates two eigenvectors that establish a two-dimensional eigenspace. The vertices that represent the spectral peaks are projected into the eigenspace and used to fit a line. In some embodiments, a second line, orthogonal to the first line, can be used to partition the eigenspace. Thus, the spectral peaks selected from the dissociation spectrum data can be classified into two or more classifications responsive to the weighted edges between the vertices representing the selected peaks.

While one skilled in the art could believe that the classification of vertices is accomplished by determining the distance between the vertices representing the spectral peaks and the artificial peaks, such a one, after reading and understanding the disclosure herein described (for example that associated with FIG. 7), will appreciate that the partitioning of the spectral peaks instead depends on the partitioning of the eigenspace responsive to the projection of the vertices within the eigenspace. The 'apply confidence-weighted classification to the spectral peaks' procedure 407 is subsequently described with respect to FIG. 6.

Next an 'adjust spectral peak intensities' procedure 409 adjusts the spectral peak intensities responsive to the results of the 'apply confidence-weighted classification to the spectral peaks' procedure 407 and, in some embodiments, responsive to the intensity ranking of the spectral peaks. This is subsequently described with respect to FIG. 7.

Once the spectral peak intensities in the vertices have been adjusted, an optional 'determine possible sequence of molecular subunits' procedure 411 can be applied to the adjusted spectral peak intensities to create possible sequences of molecular subunits that are consistent with the mass of the parent molecule and the dissociation spectrum data. In addition, or separately, an optional 'recreate spectrum' procedure 412 can recreate a mass-over-charge spectrum based on the adjusted peak intensities, which then can be used by other sequencing processes. Regardless of which combination of the optional 'determine possible sequence of molecular subunits' procedure 411 or the optional 'recreate spectrum' procedure 412 (if any) is used, a 'present data' procedure 413 can be used to present the adjusted peak intensities, the classification of the vertices, the adjusted dissociation spectrum data, and/or results of the optional processes for subsequent processing by other sequencing programs, to store, display, or otherwise present the results; or to present the results of the sequencing of the molecular subunits. One skilled in the art will understand that such a sequencer can generate more than one possible molecular subunit sequence for the parent molecule. Such a one will also understand that adjusted dissociation spectrum data can be generated from the characteristics of the vertices.

The molecular fragment classification process 400 completes through an 'end' terminal 415. One skilled in the art will understand that another spectrum can be processed by restarting the molecular fragment classification process 400. Furthermore, such a one will understand that the molecular fragment classification process 400 lends itself to parallel processor architectures.

Figure 5:
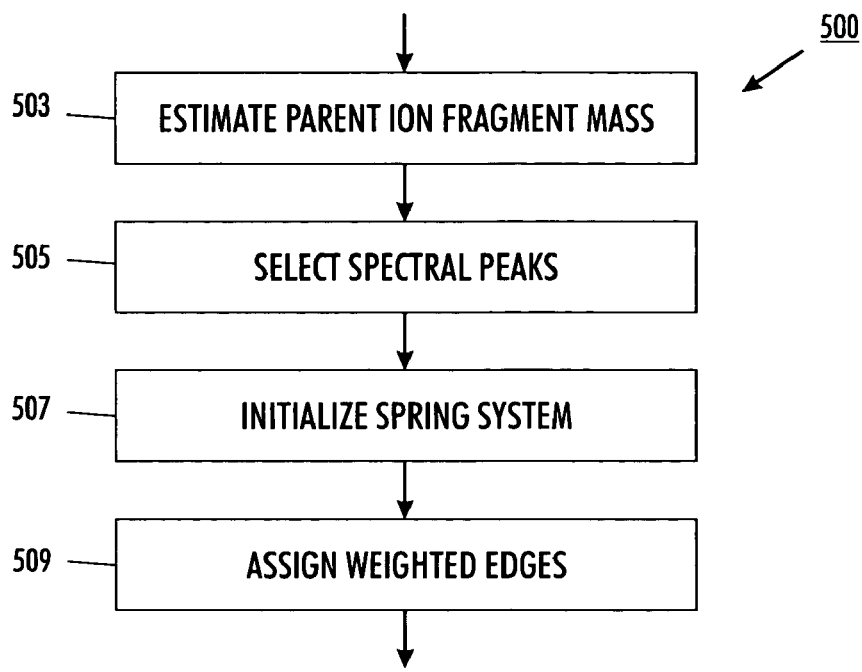
FIG. 5 illustrates one embodiment of a process that initializes a spring system responsive to dissociation spectrum data.

FIG. 5 illustrates a 'spring system initialization' process 500 that is one embodiment of the 'assign ranking and weighted edges to spectral peaks' procedure 405 of FIG. 4. The 'spring system initialization' process 500 operates on the spectral data characteristics that have been extracted from the data accessed by the 'access dissociation spectrum data' procedure 403. The 'spring system initialization' process 500 can also include an 'estimate parent ion mass' procedure 503 that estimates the mass of the parent ion using spectral peaks that appear to be complementary pairs. This estimation includes locating the nominal mass of the complex molecule as determined by the tandem mass spectrometer from data provided in the spectral data, summing spectral peak pairs, and if the sum of the spectral peak pair is within a tolerance of the nominal mass, accumulating that sum of the spectral peak pair. Once all relevant spectral peak pair sums are accumulated, a statistical analysis is performed on the accumulated spectral peak pair sums to estimate the mass of the complex molecule.

A 'select spectral peaks for spring system vertices' procedure 505 selects spectral peaks from the spectral data that have a high intensity (relative to those of similar m/z) and that do not appear to be isotopes, doubly charged, or the result of water losses (determined by the spectral peak mass and intensity relationships to nearby spectral peaks). These techniques are known to one skilled in the art.

An 'initialize spring system' procedure 507 allocates sufficient memory to represent a spring system between vertices that represent the spectral peaks selected by the 'select spectral peaks for spring system vertices' procedure 505 as well as any artificial-vertices used in the spring system. An 'assign weighted edge between adjacent vertices' procedure 509 assigns weighted edges between the vertices as is subsequently described with respect to FIG. 9 and FIG. 10.

Figure 6:
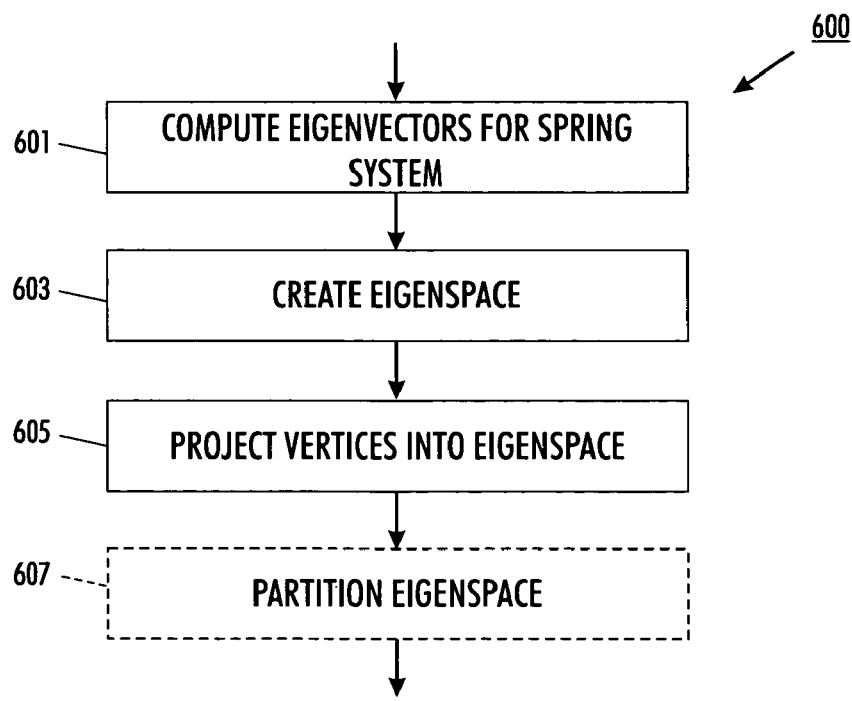
FIG. 6 illustrates one embodiment of an 'apply confidence-weighted classification' process.

FIG. 6 illustrates an 'apply confidence-weighted classification' process 600 that applies a confidence-weighted classification process (such as a spectral clustering algorithm) to the spring system that was initialized by the 'initialize spring system' procedure 507. A 'create eigenspace' procedure 603 determines the first two eigenvectors, corresponding to the smallest eigenvalues for the spring system. The first eigenvector is a solution to a least-squares problem of minimizing the potential energy of the spring system in accordance with:

$$\frac{1}{x^t D x}\left(\sum_{i,j}(x_i - x_j)^2 a_{ij}\right) = \frac{x^t(A - D)x}{x^t D x}$$

where A is the matrix of edge weights and D is a diagonal matrix containing the row sums of the absolute values of A's entries.

Figure 11:
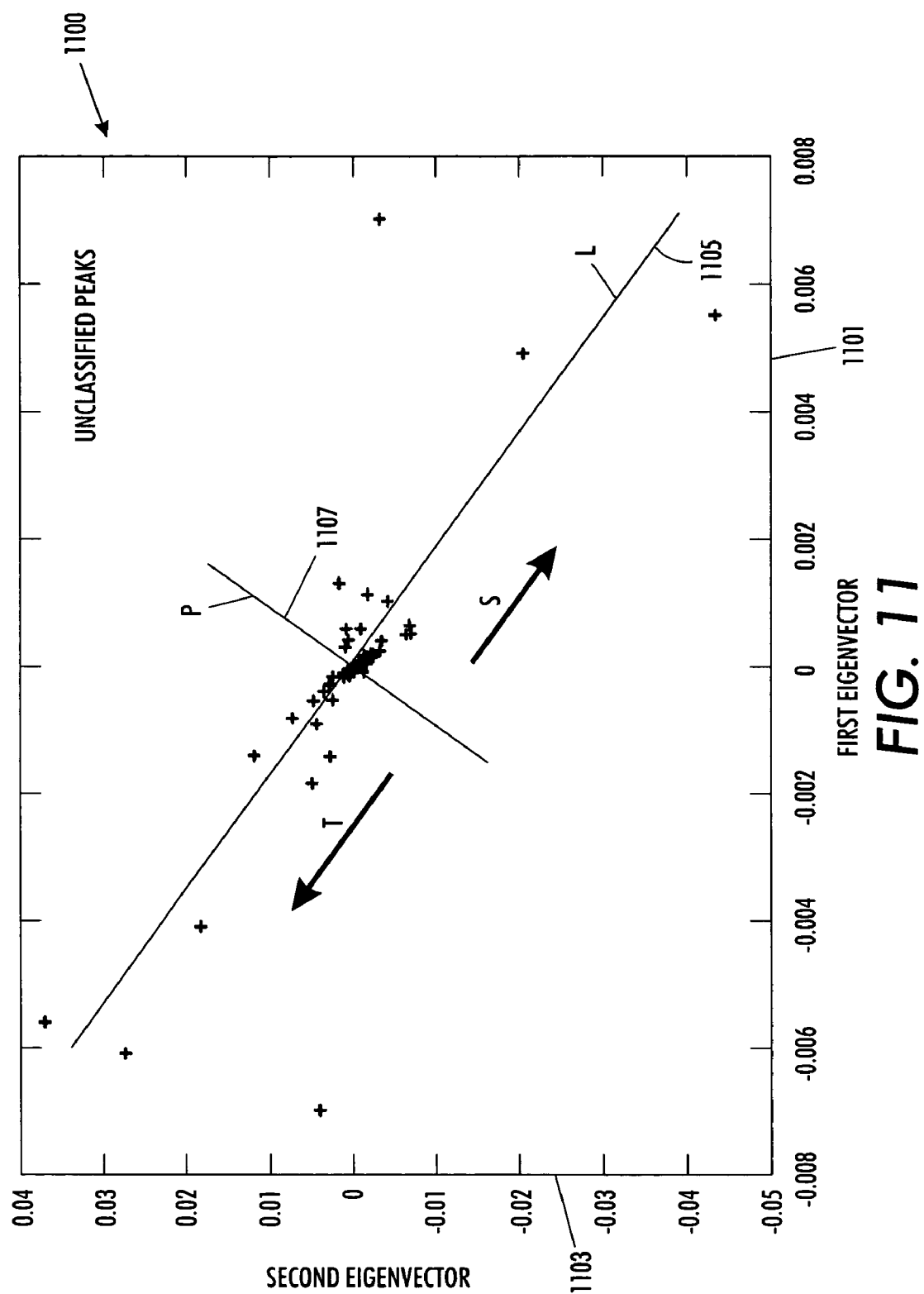
FIG. 11 illustrates a partitioned and classified two dimensional eigenspace resulting from the spectrum represented by FIG. 3.

The second eigenvector is a vibrational mode of the spring system. In one embodiment, the inventors use the first and second eigenvectors to establish a two dimensional eigenspace R that represents the spring system. A 'project vertices into eigenspace' procedure 605 then maps the vertices of the spring system into R. We next fit a reference line L to the vertices in R using, for example, a least squares fit, and then use a line P, orthogonal to L, that passes through the origin of R as a partitioning line. An example R is illustrated in FIG. 11.

Once the partitioning line P is established, an optional 'group vertices by partitioning the eigenspace' procedure 607 can classify the vertices in R into two groups (say as groups S and T) depending on which side of line P the vertex falls. For peptide spectra, vertices in the same group are likely to be the same type (for example, b-ions or y-ions). Although the vertices are separated into S and T groups, it is not known which group contains the y-ions and which group contains the b-ions. In some embodiments (for example those that sequence glycans), the eigenspace need not be partitioned because the rank of the vertex with respect to the reference line L can be sufficient to assist in the sequencing.

Figure 7:
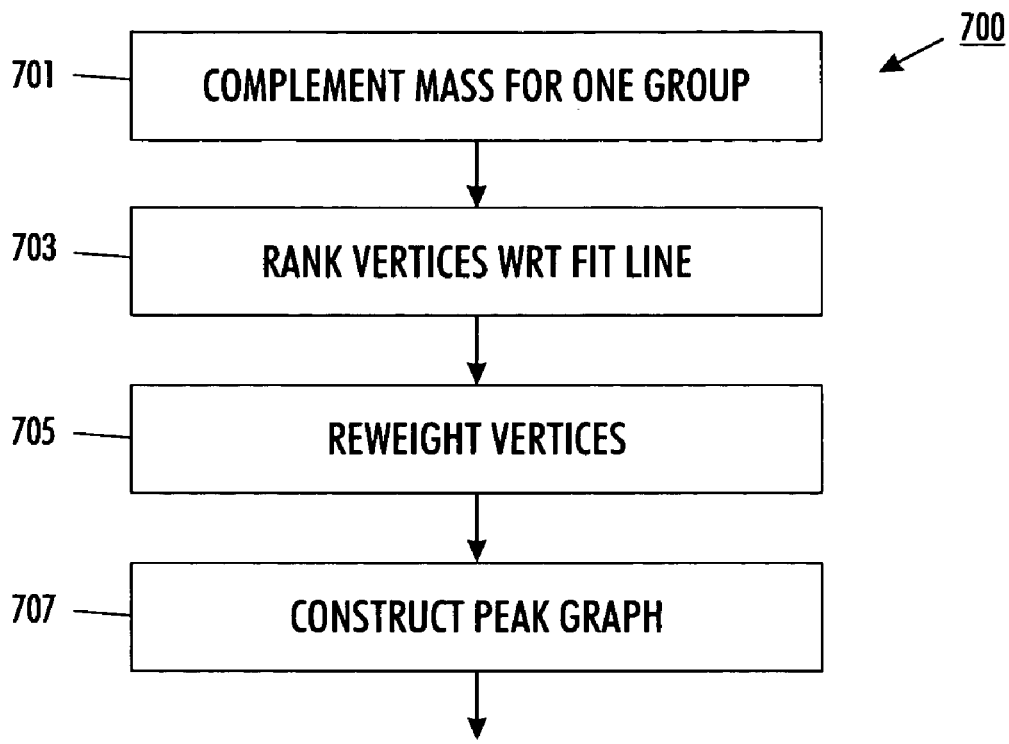
FIG. 7 illustrates one embodiment of an 'adjust spectral peak intensities' process.

FIG. 7 illustrates an 'adjust spectral peak intensities' process 700 that can be one embodiment of the 'adjust spectral peak intensities' procedure 409. The 'adjust spectral peak intensities' process 700 first applies a 'complement mass for one group' procedure 701 to complement each vertex in one of the groups by subtracting the vertex's mass from the parent molecule's mass (and optionally adjusting for any appropriate reaction mass loss/gain). Thus we can complement S to produce S'. Once we have S', a 'rank vertices with respect to fit' procedure 703 ranks the vertices with respect to line L (lrank—which is the position of the vertex projected along line L). Next, a 'reweight spectral peak' procedure 705 re-weights the spectral peaks responsive to the intensity rank (irank) and lrank:

$$\text{Intensity}(v_i) = \frac{1}{(2 \cdot lrank(v_i) + irank(v_i))}.$$

In protein and peptide analysis (where the spectra often only have two classifications (for example, y-ion and other; or b-ion and other) the 'rank vertices with respect to fit' procedure 703 limits the maximum lrank to that of the maximum lrank resulting from vertices on the positive side of L. Other types of parent molecules may not need this constraint.

In protein and peptide analysis y-ions are often preferred. Thus, additional information can be developed by including the artificial B and Y vertices (see the subsequent discussion with respect to FIG. 9) in the spring system. The half of the eigenspace that contains the artificial B vertex is the half that probably includes the b-ions, while the eigenspace half that contains the artificial Y vertex is probably the half that contains the y-ions. If the artificial B and artificial Y vertices end up in the same eigenspace partition, one can determine the distance from the partition line P to the vertices to break the tie. The inventor has determined that this method correctly identifies b-ions and y-ions at least 70% of the time. While this provides a high probability of resolution for the b/y ambiguity problem, one embodiment will still try both "y-ion half" and "b-ion half" assignments of S and T in order to capture all possible sequences (for example, see the subsequent description with respect to FIG. 8.

Next, a 'construct peak graph' procedure 707 builds a Peak graph from the vertices in S' and T with edges between two peaks that differ by the mass of one or two amino acid residues (larger amino acid masses are allowed for the initial and final gaps). The Peak graph can be presented to storage, for display, or to another procedure for subsequent processing.

Figure 8:
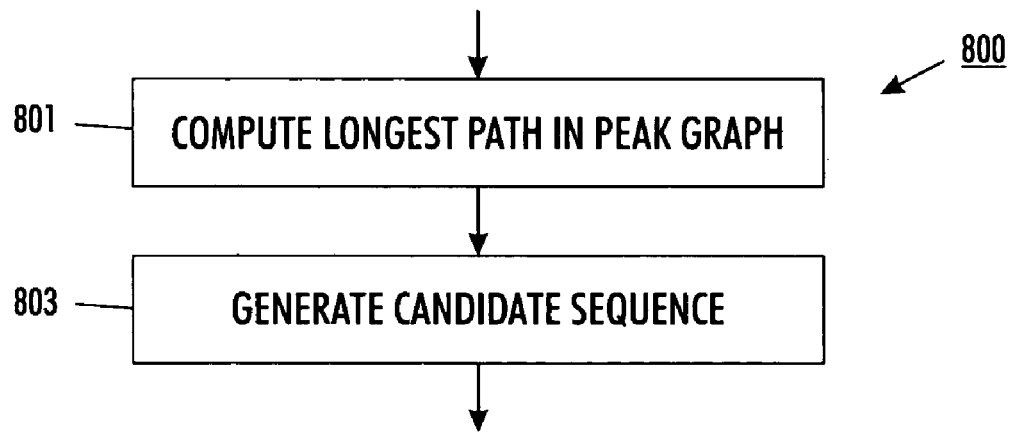
FIG. 8 illustrates a 'determine possible sequence of molecular subunits' process.

FIG. 8 illustrates a 'determine possible sequence of molecular subunits' process 800 that can use the Peak graph generated by the 'construct peak graph' procedure 707 to determine possible sequences for the parent molecule. A 'compute longest path in the Peak graph' procedure 801 uses well-known techniques for determining the longest path in the Peak graph. Once the longest path is determined, a 'generate candidate sequences' procedure 803 converts the path into candidate sequences for the complex molecule. A subsequent scoring procedure (not shown) can use techniques that are well known to one skilled in the art to rank the candidate sequences with respect to the likelihood that the sequence is correct for the parent molecule. In one embodiment, at least six sequences are generated. These six sequences result from: 1) using S as y-ions and where the sequence ends in R; 2) using S as y-ions and assuming the sequence ends in K; 3) using S as y-ions and assuming the sequence ends in an unknown letter; 4) using T as y-ions and assuming the sequence ends in R; 5) using T as y-ions and assuming the sequence ends in K; and 6) using T as y-ions and assuming the sequence ends in an unknown letter. The sequences can be presented to storage, for display, or to another procedure for subsequent processing.

Figure 9:
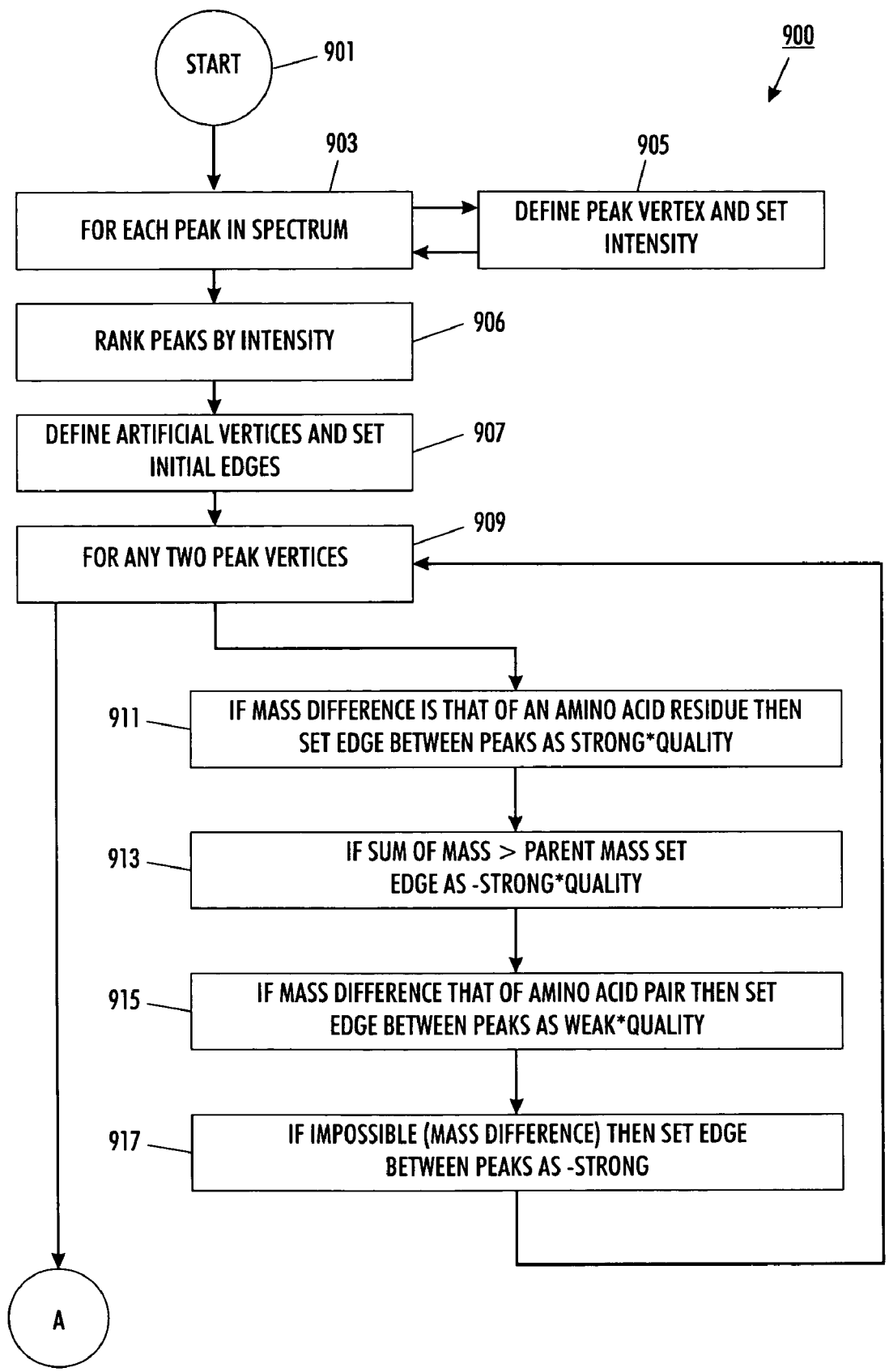
FIG. 9 illustrates a first portion of an edge-weighting process for the spring system.
Figure 10:
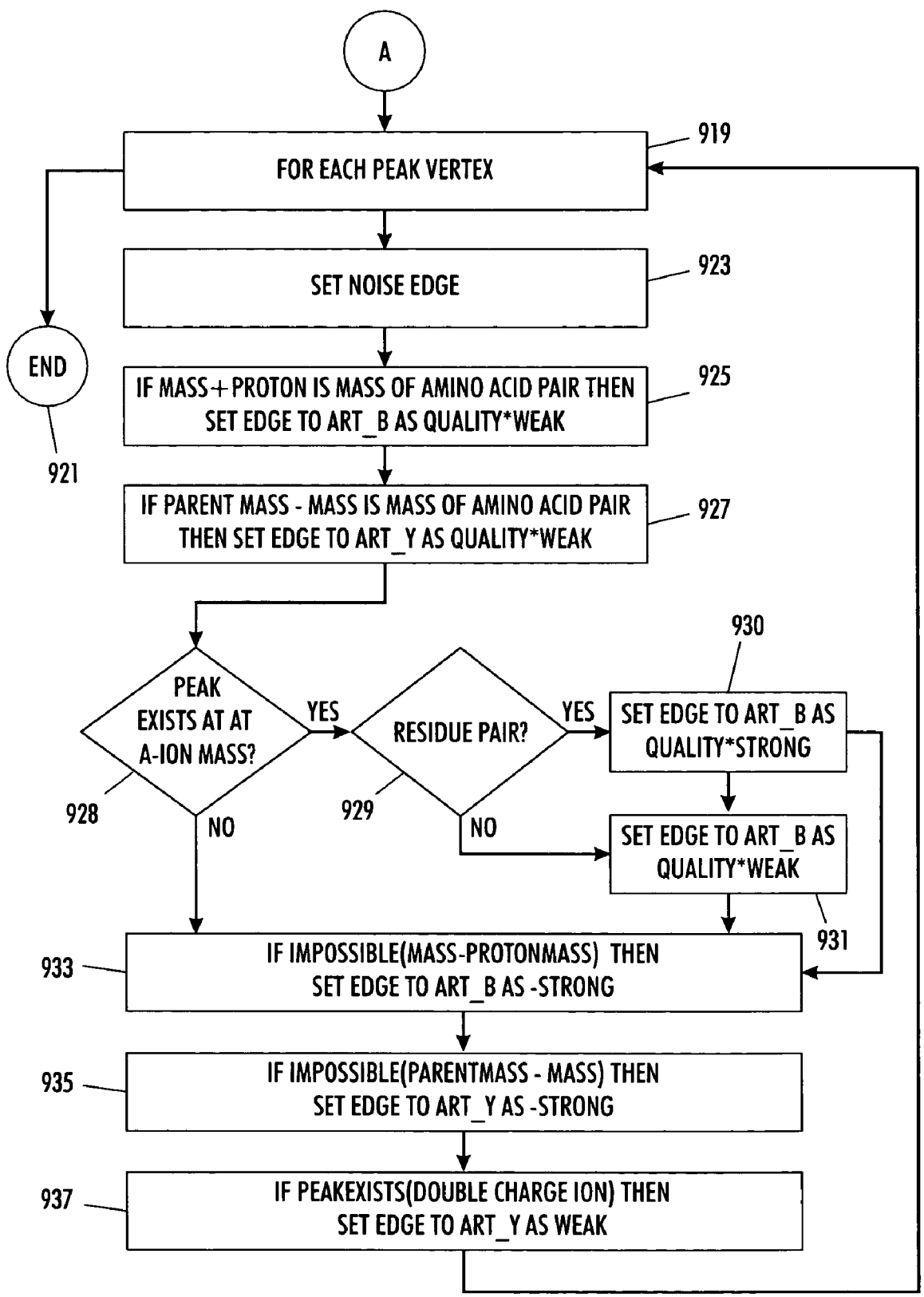
FIG. 10 illustrates a second portion of the edge-weighting process for the spring system.

FIG. 9 illustrates an edge-weighting process 900 that can be invoked at the 'assign weighted edge between adjacent vertices' procedure 509 of FIG. 5 to establish the edge weights for the spring system prior to application of the confidence-weighted classification.

The edge-weighting process 900 is illustrated by pseudocode. Pseudocode is a generic way of describing an algorithm without use of any specific programming language syntax. Pseudocode cannot be executed on a real computer, but it models and resembles real programming code. The pseudocode is provided to aid one skilled in the art understand details of the algorithms. One skilled in the art would understand how to implement these steps using any programming language or methodology. Such a one will also understand that equivalent electronics can embody the techniques described herein. Sections of the pseudocode are extracted into Tables 1-10 and some aspects of the "syntax" of the pseudocode become more clear when the code is combined from the tables.

The weighted edges establish affinities between the vertices in the spring system that represents the spectral peak intensities in the dissociation spectrum data. The edge-weighting process 900 initiates at a start terminal 901 and continues to a 'spectral peak' iteration procedure 903 that traverses the dissociation spectrum data and recognizes each relevant spectral peak. Relevant spectral peaks are, for example, those with an intensity that is above a particular threshold and/or within a range of m/z values. Once a spectral peak is recognized, an 'initialize spectral peak vertex' procedure 905 can allocate storage for the vertex and can assign the spectral peak intensity to the vertex as illustrated in Table 1.

TABLE 1

For each peak in spectrum { //extract peak info from spectrum
   New vert mz;
   mz.intensity = peakvalue;
   mz.mass = peakXposition;
}
For each mz in spectrum {mz.irank=irank(mz)}

Once all the spectral peaks are detected from the dissociation spectrum data, a 'rank spectral peaks by intensity' procedure 906 provides an intensity ranking order for each spectral peak wherein, in one embodiment, the most intense spectral peak is given the intensity rank of one, the second most intense spectral peak is given the intensity rank of two, etc.

TABLE 2

New vert Art_B;   // add artificial peaks
New vert Art_Y;
New vert Art_N;
   // init artificial peak edges
Edge(Art_B, Art_Y).weight = −2*Strong;
Edge(Art_B, Art_N).weight = −Strong;
Edge(Art_Y, Art_N).weight = −Strong;

An 'initialize artificial vertices' procedure 907 (as illustrated in Table 2) allocates at least two artificial vertices that will be associated with the two classes of ions that we are interested in. In protein and peptide analysis the two classes of ions are b-ions and y-ions. Some embodiments (such as this one) may add another vertex to help attract noise peaks. Edges are established between the artificial vertices. In one embodiment, the edge between the two classification vertices is set to repel each other. Each of the classification vertices also has repelling edges to the noise vertex if it is used.

TABLE 3

For any two mz Vsmaller and Vlarger in spectrum {
   deltaMass = Vlarger.mass − Vsmaller.mass;
   if (compareMasses(DeltaMass, AminoAcids,Quality)) {
      edge(Vlarger, Vsmaller).weight += Strong*Quality;
   }
   if(compareMasses(Vlarger+Vsmaller,ParentMass,Quality)){
      edge(Vlarger, Vsmaller).weight += −Strong*Quality;
   }
   if (compareMasses(DeltaMass,AminoAcidpairs,Quality)){
      edge (Vlarger, Vsmaller).weight += Weak*Quality;
   }
   if (impossible(deltaMass)) {
      edge(Vlarger, Vsmaller).weight += −Strong;
   }
}

A 'spectral peak pair' iteration procedure 909 (as illustrated in Table 3) then iterates once over each pair of vertices that correspond to spectral peaks in the dissociation spectrum data. As each pair of vertices is iterated, the edges between the pair are adjusted responsive to a number of conditions. For example, but without limitation, the inventors have determined that good results can be obtained for peptides by weighting the edge between the two vertices in accordance with the following.

An 'amino acid residue edge' check procedure 911 determines how closely the difference in m/z between the spectral peak pairs matches an amino acid residue. If there is a close match, a Strong edge is added between the two spectral peaks. The strength of the edge can be modified by a Quality value that represents how closely the m/z difference between the spectral peaks matches the mass of an amino acid. In the following tables, the Quality variable gives the closeness of the match between the two masses. In one embodiment, Quality equals 1.0 for a perfect match, and decreases to 0.0 at a user-defined tolerance. An appropriate tolerance for an ion-trap mass spectrometer could be 0.4 daltons while an appropriate tolerance for a QTOF instrument could be 0.1 Daltons. In the pseudocode used herein, the edge programmed-method establishes an edge with the specified weight between two vertices if no edge exists. Subsequent edge programmed-method invocations add the specified weight to the existing edge. In both cases the edge weight operand can be indicated by "+=" in the pseudocode. One skilled in the art will understand that there are many different, but equivalent, ways of weighting the edges.

A 'complementary spectral peaks edge' check procedure 913 determines whether sum of the m/z are about the same as the mass of the parent molecule. If so, the weight of the edge is reduced by –Strong (that can be modified by Quality) because the spectral peaks are likely to not have the same classification (that is, it is very likely that one spectral peak represents a b-ion and the other represents a y-ion; thus the two spectral peaks should be encouraged to be in different classifications and this is accomplished by adjusting the edge by a repulsive amount.

An 'amino acid pair' check procedure 915 determines whether the difference in m/z between the spectral peaks matches a pair of amino acid residues. If this is true, the edge is increased by Weak as adjusted by Quality.

An 'impossible mass' check procedure 917 determines whether the difference in m/z between the spectral peaks is not a residue mass or a sum of residue masses. If the difference in m/z between the spectral peaks is not a residue mass or a sum of residue masses, the edge is made less attractive by –Strong.

One skilled in the art will understand that other embodiments can use methods for defining edges other than the establishment of the weighted edge followed by modifications to that edge that are based on characteristics of the spectral peak pair. In addition, other characteristics of the spectral peak pair, or relationships to a third spectral peak, can also be incorporated into the weighted edge between the spectral peak pair.

Once the edges for all spectral peak pairs have been established, the edge-weighting process 900 continues to adjust the edges for each spectral peak (see FIG. 10) as follows:

TABLE 4

For each mz Vthis in spectrum {
    NoiseEdge=(Strong/rankMax)*min(Vthis.irank–1,rankMax);
    edge(Vthis, Art_N).weight += NoiseEdge;

Table 4 illustrates a 'spectral peak' iteration procedure 919 that establishes an iteration over vertices that represent the spectral peaks in the dissociation spectrum data. After all selected vertices have been processed, the edge-weighting process 900 completes through an 'end' terminal 921. As each vertex is processed, a 'noise edge' procedure 923 adds an edge between the processed vertex representing a spectral peak and the artificial vertex for noise. The strength of the edge is Strong divided by the maximum intensity rank as adjusted by the rank of the spectral peak. Thus, (assuming rankMax is 100) the highest intensity spectral peak has no edge to noise. While the second highest intensity spectral peak has an edge to noise of $1/100$ Strong and the nth intense spectral peak (where n is rankMax+1 or higher) would be Strong.

TABLE 5

If (compareMasses(Vthis.mass–protonMass,
    AminoAcidpairs,Quality)){
    edge(Vthis, Art_B).weight += Quality*Weak;
}

Next, a 'b-ion residue pair' check procedure 925 (illustrated by Table 5) determines whether the spectral peak's m/z minus the proton mass matches an amino acid pair. If so, the weighted edge to Art_B is increased by Weak as adjusted by the mass accuracy (Quality) which is how closely the peak's m/z matches the mass of a pair of amino acids.

TABLE 6

If (compareMasses(ParentMass–Vthis.mass,
    AminoAcidpairs,Quality)) {
    edge(Vthis, Art_Y).weight += Quality*Weak;
}

Next, a 'y-ion residue pair' check procedure 927 (illustrated by Table 6) determines whether the peak's m/z subtracted from the parent molecule's mass matches an amino acid pair. If this is true, the edge weight to Art_Y is increased by Weak as adjusted by Quality.

TABLE 7

If (peakExists(Vthis.mass – 27.995,quality)) {
    if(compareMasses(Vthis.mass–protonMass,
        AminoAcidpairs,Quality)) {
        edge(Vthis, Art_B).weight += Strong*Quality;
    } else {
        edge(Vthis,Art_B).weight += Quality*Weak;
    }
}

An 'a-ion detection' conditional procedure 928 (illustrated by Table 7) first determines if a peak exists that is 27.995 less than the current peak (thus indicating that the current spectral peak is a result of an additional carbon monoxide attached to the fragment). If so, a 'residue Pair' conditional procedure 929 determines if the spectral peak mass minus a proton matches the mass of an amino acid pair and if so a 'strong edge' procedure 930 increases the edge between the spectral peak and Art_B by Strong as adjusted by Quality to the mass of a pair of amino acids.

If the 'residue Pair' conditional procedure 929 determines that the spectral peak's mass minus a proton mass does not match an amino acid pair, then a 'weak edge' procedure 931 increases the edge between the spectral peak and Art_B by Weak as adjusted by the Quality of the spectral peak to the mass of a pair of amino acids.

TABLE 8 if (impossible(Vthis.mass–protonMass)){
    edge(Vthis,Art_B).weight += –Strong;
}

An 'impossible b-ion' check procedure 933 (illustrated by Table 8) determines whether the m/z of the spectral peak minus the mass of a proton is not the mass of a low mass ion. If this is so, the edge's attraction between this vertex and Art_B is reduced by Strong.

TABLE 9

```
if (impossible(ParentMass–Vthis.mass)){
    edge(Vthis,Art_Y).weight += –Strong
}
```

An 'impossible y-ion' check procedure 935 (illustrated by Table 9) determines whether the complement of the m/z of the spectral peak is not the mass of a low mass ion. If so, the attraction of the edge between the vertex and Art_Y is reduced by Strong.

A 'double charge ion' check procedure 937 (illustrated by Table 10) determines if a spectral peak exists at the m/z that is half of the m/z of the spectral peak mass plus the proton mass. If such a spectral peak exists, then the edge from the vertex to Art_Y is increased by Weak.

TABLE 10

```
if (peakexists((Vthis.mass+protonMass)/2,quality)) {
    edge(Vthis,Art_Y).weight += Weak;
  }
}
```

One skilled in the art would understand that additional edge adjustments could be made depending on how well the spectral peak's mass matches the mass of an amino acid triple.

How do we set Weak and Strong? We set Strong to be 6 times Weak, because (at 0.2 Dalton resolution) there are about 6 times as many distinct residue-pair masses as distinct residue masses. In addition, we have determined that graph partitioning is very robust under different weights and that the results are not very sensitive to changes in the weights.

Finally, why is the negative weight between two peaks separated by an impossible mass only Strong rather than much stronger or even infinite? If we use extremely strong impossible edges, then a chemical noise peak with, for example, 3 impossible edges to y-ion peaks and 5 impossible edges to b-ion peaks will be pushed far to the T side (where it will then push away some real y-ions).

FIG. 11 illustrates a two dimensional eigenspace R 1100 using a first eigenvector coordinate 1101 as one coordinate of the eigenspace and a second eigenvector coordinate 1103 as the other coordinate. As was described with respect to FIG. 6, a line L 1105 fit to the vertices' locations in the eigenspace is created and a partitioning line P 1107 orthogonal to the line L 1105 is located at the origin of the two dimensional eigenspace R 1100. Groups S and T are assigned to either side of the partitioning line P 1107.

Figure 12:
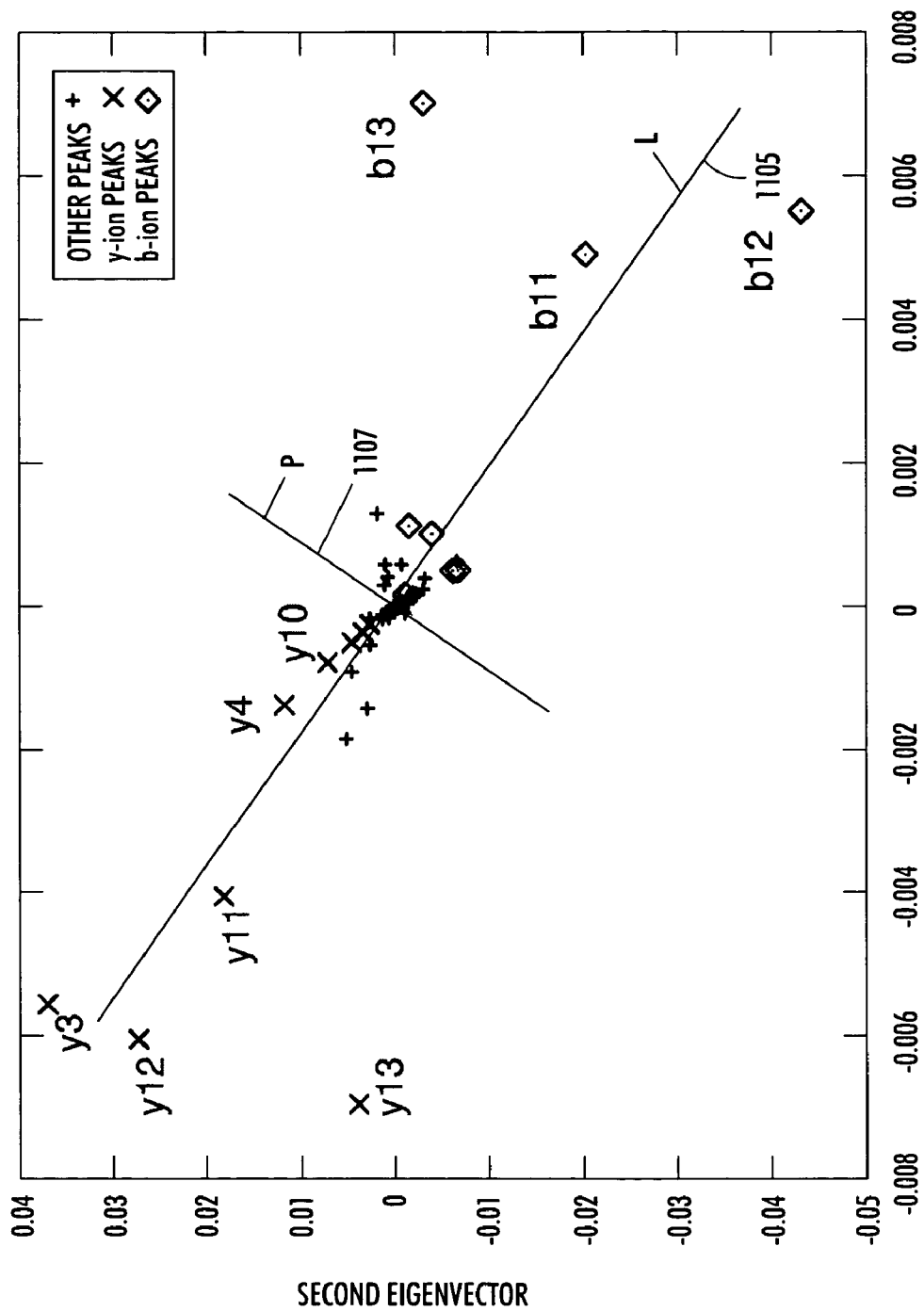
FIG. 12 illustrates a partitioned and identified two dimensional eigenspace resulting from the sequencing of the vertices classified as shown in FIG. 11.

FIG. 12 illustrates the identification of the vertices resulting from sequencing the spectrum using the techniques disclosed herein for classifying the spectrum's spectral peaks.

Figure 13:
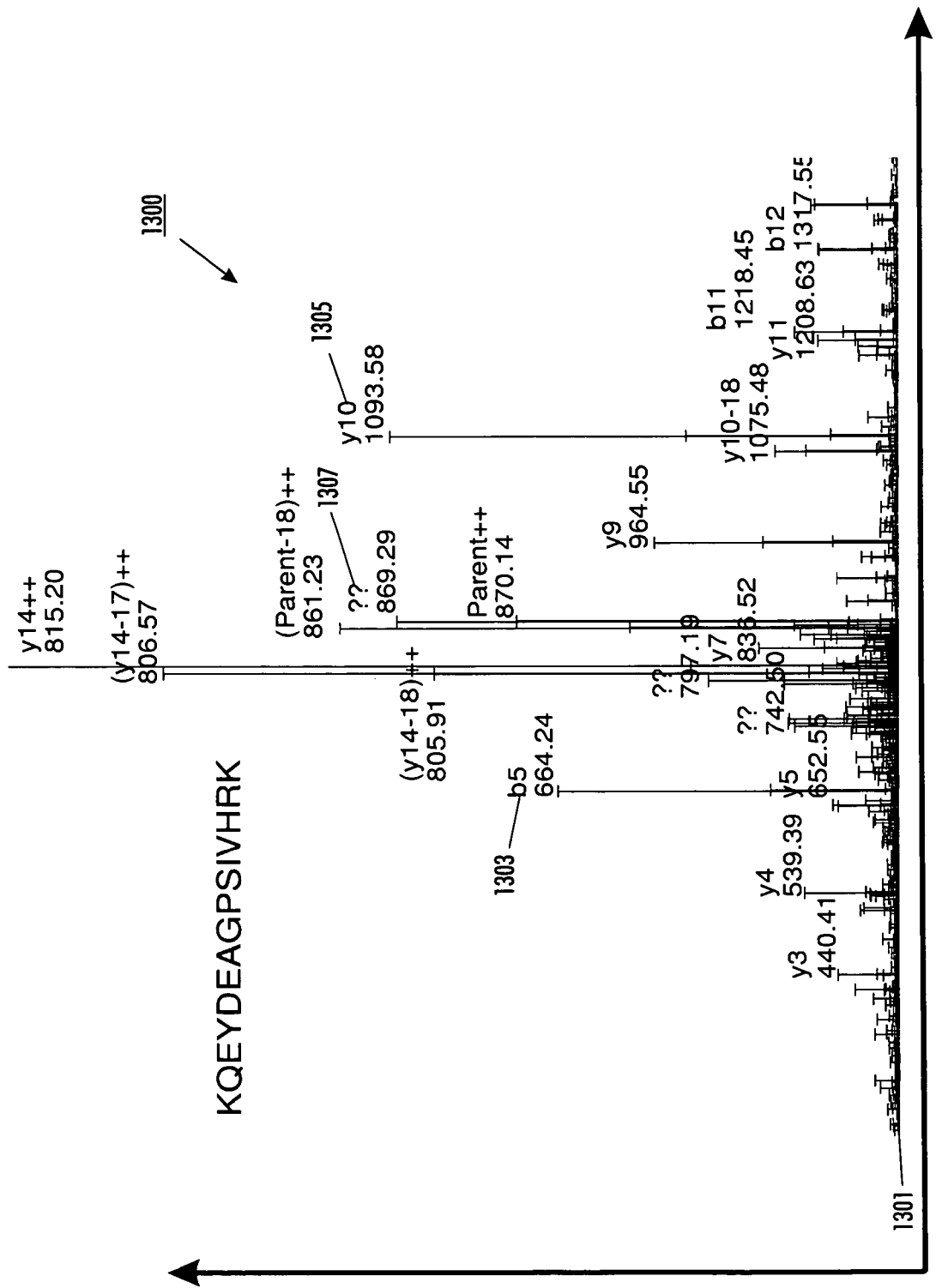
FIG. 13 illustrates a sequenced dissociation spectrum data that can result from a tandem mass spectrometer spectrum that has been analyzed by the process of FIG. 4 and that generated the eigenspace of FIG. 11.

FIG. 13 illustrates an analyzed dissociation spectrum data of the peptide KQEYDEAGPSIVHRK 1300. As in FIG. 3, the spectrum includes a plurality of m/z mass spectral peaks 1301. However, now the spectral peaks can be further identified as (for example) a b-ion spectral peak 1303, a y-ion spectral peak 1305, and a noise peak 1307

One skilled in the art will understand that the edge method will create an edge of the specified weight if no edge previously existed between the vertices or will modify an existing edge by the supplied weight.

One skilled in the art will understand that the techniques described herein apply generally to a parent molecule and molecular subunits as well as the peptides and amino acids used to illustrate one embodiment. In particular, a parent molecule can be at least one of a polymer, a lipid, a protein, a peptide and a glycan as well as other molecules that comprise a number of molecular subunits separated by cleavage sites each of which connect one molecular subunit with another molecular subunit.

One skilled in the art will understand that the disclosed technology allows provides advances in the sequencing of complex molecules. Furthermore, from the foregoing, it will be appreciated that the efficient classification or partial classification of spectral peaks has (without limitation) the following advantages:

1) A de novo sequencer can now generate fewer candidate sequences (thus the probability of each sequence being correct can be much higher);

2) Because fewer sequences are generated, a de novo sequencer using the disclosed technology provides a faster generation of a set of sequences that is likely to contain the correct sequence;

3) Because a de novo sequencer using the disclosed technology is faster and more accurate than the existing techniques, such a de novo sequencer can now sequence much longer peptides and even complete proteins;

4) One embodiment modifies spectral peak intensities responsive to the peak classification. This modified spectrum can be presented to existing sequencing programs for processing. Because the modified spectrum is less ambiguous, these programs will be more likely to generate a correct sequence;

5) Increased accuracy of de novo sequencers because of the remarkable success at solving the b/y ambiguity problem associated with dissociation spectra of proteins and peptides.

6) Provides a computationally efficient and robust solution to the peak classification problem.

7) The strongest class (largest number of intense peaks) repels all the others, and the attraction between noise peaks (such as internal fragments that are separated by residue masses) aids in the classification of the peaks.

8) Some spectra have more than three classes; this can occur if there is more than one peptide or if there are many internal fragments (contiguous subsequences from the middle of the residue sequence). Such spectra are difficult for the pure longest-path prior approaches, which can easily "jump tracks" from one peptide to another. This problem is reduced by robust classification of the spectral peaks.

Although the claimed technology has been described in terms of the presently preferred embodiments, one skilled in the art will understand that various modifications and alterations may be made without departing from the scope of the claims. Accordingly, the claims are not to be limited to the particular embodiments discussed herein.

What is claimed follows:

1. A computer controlled method comprising:
   accessing dissociation spectrum data comprising a plurality of spectral peaks representing a plurality of fragments of a parent molecule, said parent molecule comprising a plurality of molecular subunits and a plurality of cleavage sites, each of said plurality of cleavage sites connecting a first one of said plurality of molecular subunits and a second one of said plurality of molecular subunits, said plurality of spectral peaks associated with a respective plurality of peak intensities;

representing a portion of said plurality of spectral peaks as a plurality of vertices;

assigning a plurality of weighted edges to said plurality of vertices;

applying a confidence-weighted classification to said plurality of vertices responsive to said plurality of weighted edges;

adjusting said respective plurality of peak intensities responsive to the step of applying;

and presenting said respective plurality of peak intensities.

2. The computer controlled method of claim 1, wherein the step of presenting further comprises determining at least one possible molecular subunit sequence for a portion of said parent molecule.

3. The computer controlled method of claim 2, wherein the step of applying classifies said portion of said plurality of vertices into a plurality of classes, said plurality of classes representing a first class of spectral peaks and a second class of spectral peaks;

and wherein the step of presenting further comprises complementing the first class relative to the mass of said parent molecule that yielded said dissociation spectrum data.

4. The computer controlled method of claim 1, wherein the step of presenting further comprises:

generating a processed spectrum responsive to the step of adjusting;

and providing said processed spectrum to at least a portion of a sequencing program.

5. The computer controlled method of claim 1, wherein the step of presenting further comprises identifying one or more of said plurality of spectral peaks in accordance with the step of adjusting.

6. The computer controlled method of claim 1, wherein said parent molecule is one or more selected from a group consisting of a polymer, a lipid, a protein, a peptide and a glycan.

7. The computer controlled method of claim 1, wherein said parent molecule is a protein or peptide and said plurality of molecular subunits are amino acids.

8. The computer controlled method of claim 1, wherein the step of applying further comprises:

generating a graph comprising said plurality of vertices representing said portion of said plurality of spectral peaks and including at least one artificial vertex;

said graph further comprising said plurality of weighted edges wherein said plurality of weighted edges represent a plurality of affinities between said plurality of vertices.

9. The computer controlled method of claim 8, wherein said graph is represented by a matrix wherein said plurality of weighted edges of the graph are off-diagonal values of said matrix and the diagonal values of said matrix are the sums of the absolute values of the corresponding rows of said matrix;

and wherein the step of applying further comprises:

computing a plurality of eigenvectors for the generalized eigenvector problem represented by said matrix;

and weighting the $i^{th}$ vertex according to a combination of the $i^{th}$ coordinates in an eigenspace defined by said plurality of eigenvectors.

10. A computer program product comprising:

a computer-usable data carrier storing instructions that, when executed by a computer, cause said computer to perform a method comprising:

accessing dissociation spectrum data comprising a plurality of spectral peaks representing a plurality of fragments of a parent molecule, said parent molecule comprising a plurality of molecular subunits and a plurality of cleavage sites, each of said plurality of cleavage sites connecting a first one of said plurality of molecular subunits and a second one of said plurality of molecular subunits, said plurality of spectral peaks associated with a respective plurality of peak intensities;

representing a portion of said plurality of spectral peaks as a plurality of vertices;

assigning a plurality of weighted edges to said plurality of vertices;

applying a confidence-weighted classification to said plurality of vertices responsive to said plurality of weighted edges;

adjusting said respective plurality of peak intensities responsive to the step of applying;

and presenting said respective plurality of peak intensities.

11. The computer program product of claim 10, wherein the step of presenting further comprises determining at least one possible molecular subunit sequence for a portion of said parent molecule.

12. The computer program product of claim 11, wherein the step of applying classifies said portion of said plurality of vertices into a plurality of classes, said plurality of classes representing a first class of spectral peaks and a second class of spectral peaks;

and wherein the step of presenting further comprises complementing the first class relative to the mass of said parent molecule that yielded said dissociation spectrum data.

13. The computer program product of claim 10, wherein the step of presenting further comprises:

generating a processed spectrum responsive to the step of adjusting;

and providing said processed spectrum to at least a portion of a sequencing program.

14. The computer program product of claim 10, wherein the step of presenting further comprises identifying one or more of said plurality of spectral peaks in accordance with the step of adjusting.

15. The computer program product of claim 10, wherein said parent molecule is one or more selected from a group consisting of a polymer, a lipid, a protein, a peptide and a glycan.

16. The computer program product of claim 10, wherein said parent molecule is a protein or peptide and said plurality of molecular subunits are amino acids.

17. The computer program product of claim 10, wherein the step of applying further comprises:

generating a graph comprising said plurality of vertices representing said portion of said plurality of spectral peaks and including at least one artificial vertex;

said graph further comprising said plurality of weighted edges wherein said plurality of weighted edges represent a plurality of affinities between said plurality of vertices.

18. The computer program product of claim 17, wherein said graph is represented by a matrix wherein said plurality of weighted edges of the graph are off-diagonal values of said matrix and the diagonal values of said matrix are the sums of the absolute values of the corresponding rows of said matrix;

and wherein the step of applying further comprises:

computing a plurality of eigenvectors for the generalized eigenvector problem represented by said matrix;

and weighting the $i^{th}$ vertex according to a combination of the $i^{th}$ coordinates in an eigenspace defined by said plurality of eigenvectors.

19. An apparatus comprising:

a spectrum access logic configured to access dissociation spectrum data comprising a plurality of spectral peaks representing a plurality of fragments of a parent molecule, said parent molecule comprising a plurality of molecular subunits and a plurality of cleavage sites, each of said plurality of cleavage sites connecting a first one of said plurality of molecular subunits and a second one of said plurality of molecular subunits, said plurality of spectral peaks associated with a respective plurality of peak intensities;

a peak selection logic configured to represent a portion of said plurality of spectral peaks accessed by the spectrum access logic as a plurality of vertices;

an edge weight assignment logic configured to assign a plurality of weighted edges to said plurality of vertices selected by the peak selection logic;

a classification logic configured to apply a confidence-weighted classification to said plurality of vertices responsive to said plurality of weighted edges;

an adjustment logic configured to adjust said respective plurality of peak intensities responsive to the classification logic;

and a presentation logic configured to present said respective plurality of peak intensities by storing representations of a spectrum with spectral peaks identified by the use of the technology or displaying data from such a spectrum; displaying or storing molecular sequences identified by the use of the technology; passing data representing or derived from the use of the technology to another system (for example, a computer via use of a computer-usable data carrier such as tangible storage devices or a network—and/or using remote procedure call protocols), to another procedure, and/or to a programmed routine.

20. The apparatus of claim 19, wherein the presentation logic further comprises a sequence logic configured to determine at least one possible molecular subunit sequence for a portion of said parent molecule.

21. The apparatus of claim 20, wherein the classification logic classifies said portion of said plurality of vertices into a plurality of classes, said plurality of classes representing a first class of spectral peaks and a second class of spectral peaks;

and wherein the presentation logic further comprises a complementation logic configured to complement the first class relative to the mass of said parent molecule that yielded said dissociation spectrum data.

22. The apparatus of claim 19, wherein the presentation logic further comprises:

a regeneration logic configured to generate a processed spectrum responsive to the adjustment logic;

and an output logic configured to provide said processed spectrum to at least a portion of a sequencing program.

23. The apparatus of claim 19, wherein the presentation logic further comprises an ion identification logic configured to identify one or more of said plurality of spectral peaks in accordance with the adjustment logic.

24. The apparatus of claim 19, wherein said parent molecule is one or more selected from a group consisting of a polymer, a lipid, a protein, a peptide and a glycan.

25. The apparatus of claim 19, wherein said parent molecule is a protein or peptide and said plurality of molecular subunits are amino acids.

26. The apparatus of claim 19, wherein the classification logic further comprises:

a graph generation logic configured to generate a graph comprising said plurality of vertices representing said portion of said plurality of spectral peaks and including at least one artificial vertex;

said graph further comprising said plurality of weighted edges wherein said plurality of weighted edges represent a plurality of affinities between said plurality of vertices.

27. The apparatus of claim 26, wherein said graph is represented by a matrix wherein said plurality of weighted edges of the graph are off-diagonal values of said matrix and the diagonal values of said matrix are the sums of the absolute values of the corresponding rows of said matrix;

and wherein the classification logic further comprises:

an eigenvector solution logic configured to compute a plurality of eigenvectors for the generalized eigenvector problem represented by said matrix;

and a vertex evaluation logic configured to weight the $i^{th}$ vertex according to a combination of the $i^{th}$ coordinates in an eigenspace defined by said plurality of eigenvectors.

28. The apparatus of claim 19, further comprising a tandem mass spectrometer.

* * * * *